United States Patent
Becker et al.

(10) Patent No.: US 10,478,608 B2
(45) Date of Patent: Nov. 19, 2019

(54) VALVE DEVICE WITH ELASTICALLY PRETENSIONED CLOSURE ELEMENT FOR A MEDICAL SYSTEM

(71) Applicant: Fresenius Kabi Deutschland GMBH, Bad Homburg (DE)

(72) Inventors: Michael Becker, Knittlingen (DE); Barbara Amon, Idstein (DE); Benjamin Schafer, Hohenahr (DE); Leo Zeimetz, Buttelborn (DE); Matthias Rau, Wiesbaden (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 31 days.

(21) Appl. No.: 15/122,872

(22) PCT Filed: Feb. 25, 2015

(86) PCT No.: PCT/EP2015/053918
§ 371 (c)(1),
(2) Date: Aug. 31, 2016

(87) PCT Pub. No.: WO2015/139925
PCT Pub. Date: Sep. 24, 2015

(65) Prior Publication Data
US 2017/0056588 A1    Mar. 2, 2017

(30) Foreign Application Priority Data
Mar. 19, 2014    (EP) .................................... 14160703

(51) Int. Cl.
*A61M 39/22*    (2006.01)
*A61M 5/168*    (2006.01)

(52) U.S. Cl.
CPC ........ *A61M 39/22* (2013.01); *A61M 5/16813* (2013.01); *A61M 2039/226* (2013.01)

(58) Field of Classification Search
CPC .......... A61M 5/16813; A61M 5/16881; A61M 39/22; A61M 2039/226; F16K 7/16
See application file for complete search history.

(56) References Cited

U.S. PATENT DOCUMENTS 4,044,998 A  *  8/1977  Giese ........................ F16K 1/34
                                                      251/331
4,703,775 A  * 11/1987  Pastrone ........... A61M 5/16877
                                                      137/625.3

(Continued)

FOREIGN PATENT DOCUMENTS

| EP | 2433550 A1 | 3/2012 |
| EP | 2526992 A1 | 11/2012 |
| WO | WO02/09804 A1 | 2/2002 |

OTHER PUBLICATIONS

International Search Report for International Application No. PCT/EP2015/053918, dated Apr. 28, 2015.

(Continued)

*Primary Examiner* — Shefali D Patel
(74) *Attorney, Agent, or Firm* — Cook Alex Ltd.

(57) ABSTRACT

A valve device (1) for a medical system comprises a valve housing (10), an inlet port (102) arranged on the valve housing (10), an outlet port (103) arranged on the valve housing (10), a flow duct (12) extending through the valve housing (10) connecting the inlet port (102) and the outlet port (103) to allow for a fluid flow (P) through the valve housing between the inlet port (102) and the outlet port (103), and a closure element (11) arranged on the valve housing (10) for selectively opening and closing the flow duct (12). Herein, the closure element (11) is displaceable along a displacement direction (A) relative to the valve housing (10) between a closed position in which the flow duct (12) is closed for preventing the fluid flow (P) from the inlet port (102) to the outlet port (103) and an opened (Continued)

position in which the flow duct (12) is opened for allowing the fluid flow (P) from the inlet port (102) to the outlet port (103), wherein the closure element (11) is elastically pretensioned towards the closed position. In this way the valve device is provided which allows for an optimized integration into a medical device such as an infusion line or an infusion pump.

15 Claims, 5 Drawing Sheets

(56) References Cited

U.S. PATENT DOCUMENTS

| 8,316,878 B2* | 11/2012 | Lodolo | F16K 31/385 |
| | | | 137/315.05 |
| 2002/0004015 A1* | 1/2002 | Carlisle | A61M 5/14224 |
| | | | 417/479 |
| 2010/0298783 A1* | 11/2010 | Chang | A61M 1/0043 |
| | | | 604/256 |

OTHER PUBLICATIONS

Written Opinion of the International Searching Authority for International Application No. PCT/EP2015/053918, dated Apr. 28, 2015.

* cited by examiner

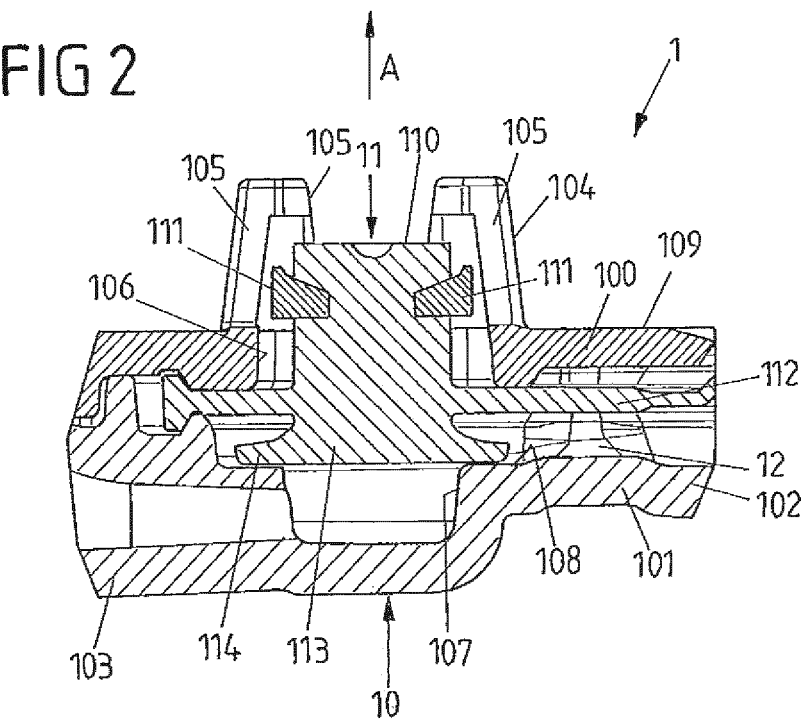
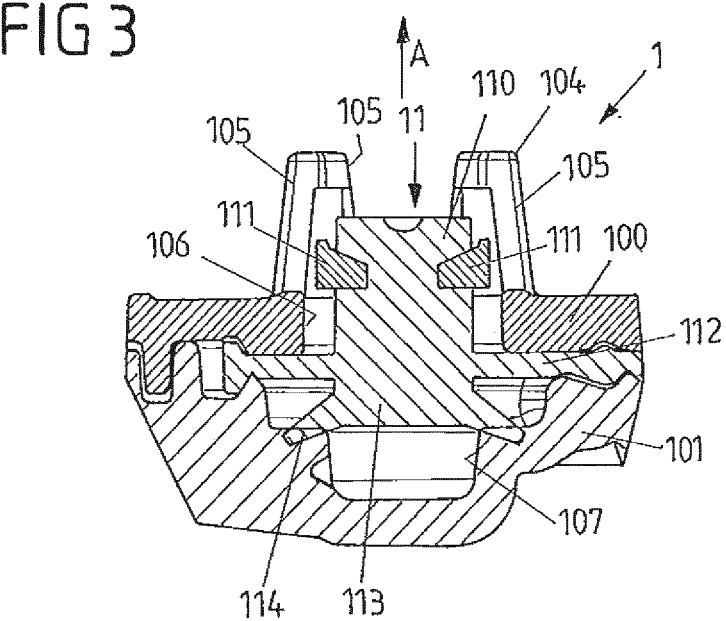

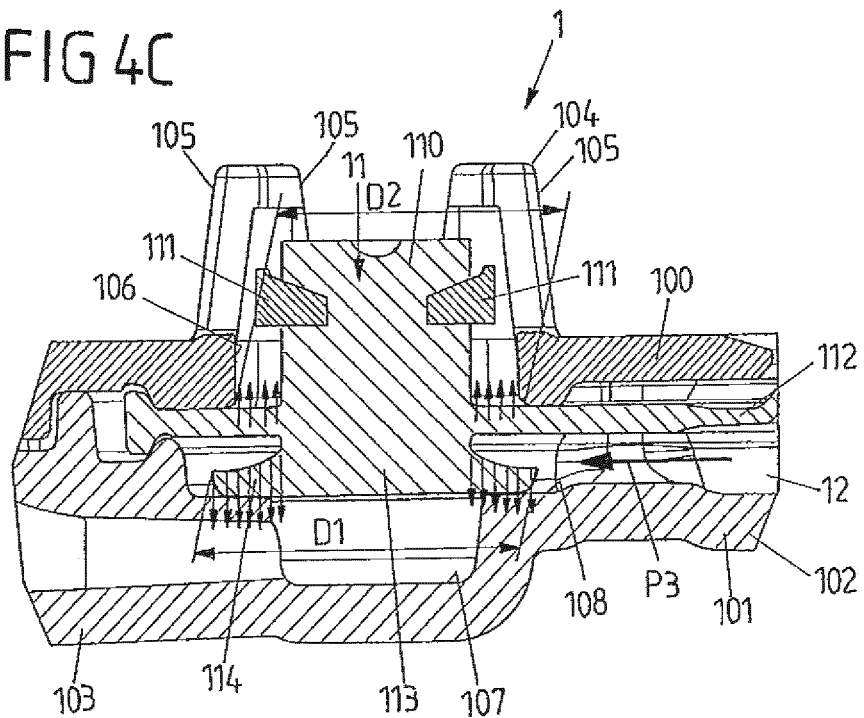
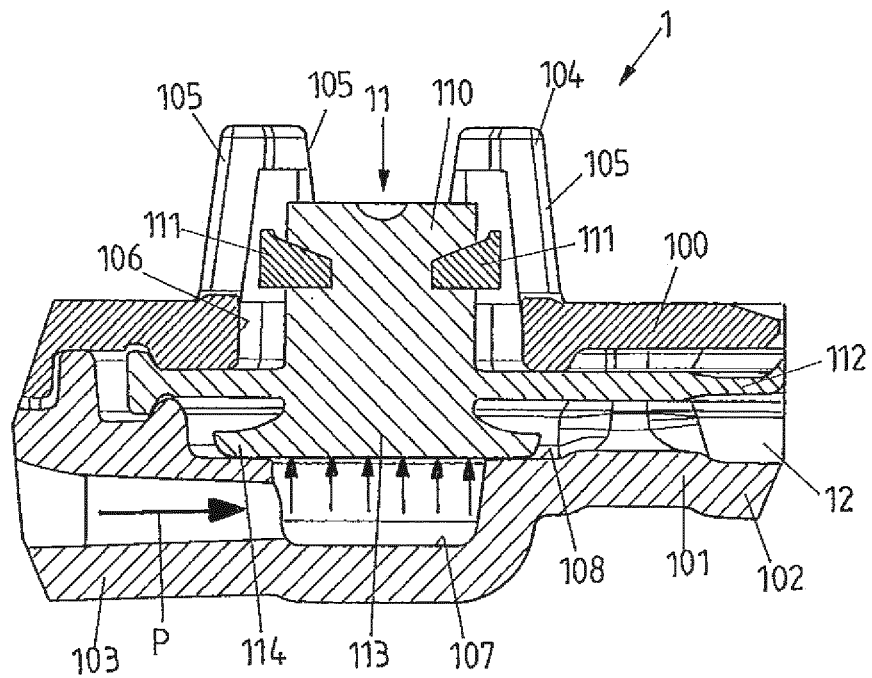

VALVE DEVICE WITH ELASTICALLY PRETENSIONED CLOSURE ELEMENT FOR A MEDICAL SYSTEM

Application No. PCT/EP2015/053918, filed Feb. 25, 2015, which claims the benefit of and priority to European Patent Application No. 14160703.6, filed Mar. 19, 2014, the contents of both of which are hereby incorporated herein by reference.

BACKGROUND

The invention relates to a valve device for a medical system according to the preamble of claim 1 and a method for operating valve device.

Such a valve device comprises a valve housing, an inlet port arranged on the valve housing, an outlet port arranged on the valve housing, a flow duct extending through the valve housing connecting the inlet port and the outlet port to allow a fluid flow through the valve housing between the inlet port and the outlet port, and a closure element arranged on the valve housing for selectively opening and closing the flow duct.

A valve device of this kind may for example be used in an infusion line for infusing medical liquids, e.g. assisted by an infusion pump, to a patient. A valve device of this kind may for example be integrated in an infusion line or may be integrated into an infusion pump or into entirely different medical devices.

Valve devices of the kind described herein serve to prevent, in a closed position, a fluid flow through for example an infusion line. Conventionally, clamping elements such as Roberts clamps may be used on infusion lines preventing a fluid flow through an infusion line by clamping off the infusion tube. Other means for selectively controlling a fluid flow through an infusion line or a multiplicity of infusion lines include for example so-called multiple-way cocks (also called selector valves) which allow for a selective establishing of flow ducts.

There is a desire for other solutions for selectively controlling a fluid flow through a flow duct. There, in particular, is a desire for a valve device allowing for an easy integration into functional groups of medical systems such as infusion lines or infusion pumps. Furthermore, there is a desire for a valve device which can be miniaturized to allow for example for integration into micro-components of medical devices.

SUMMARY

It is an object of the invention to provide a valve device and a method for operating a valve device which allow for an optimized integration into medical devices such as infusion lines or infusion pumps.

This object is achieved by means of a valve device comprising the features of claim 1.

Accordingly, the closure element is displaceable along a displacement direction relative to the valve housing between a closed position in which the flow duct is closed for preventing a fluid flow from the inlet port to the outlet port and an opened position in which the flow duct is opened for allowing a fluid flow from the inlet port to the outlet port, wherein the closure element is elastically pretensioned towards the closed position.

The instant invention is based on the idea to use a closure element which is displaceable along a displacement direction relative to the valve housing for selectively closing and opening the valve device. The closure element hence is arranged on the valve housing and can be moved relative to the valve housing by displacing it along the displacement direction between a closed position in which the flow duct is closed and an opened position in which the flow duct is open. By moving the closure element, hence, the flow duct extending between the inlet port and the outlet port can selectively be opened or closed.

Herein, the closure element is elastically pretensioned towards the closed position. For this, the closure element is arranged in an elastically pretensioned fashion on the valve housing, wherein a pretensioning force acts towards the closed position such that without actuating the closure element the closure element tends to assume its closed position, thus closing off the flow duct and hence preventing a fluid flow through the valve device.

In a non-actuated state, in which the closure element is not actuated for opening the valve device, the valve device hence is closed such that no fluid can pass from the inlet port to the outlet port. Only upon actuating the closure element by displacing it in the displacement direction to move it from its closed position into its opened position the valve device is opened, hence allowing for a fluid flow from the inlet port to the outlet port.

If the valve device is integrated for example into an infusion line, the valve device in a non-actuated state closes off the infusion line, hence preventing a fluid flow through the infusion line. Upon actuating the closure element, the valve device is opened, thus allowing for a fluid flow through the infusion line, which for example may be driven by a feed pump or by gravity from an inlet-side liquid container such as a flexible bag towards an outlet-side infusion location for infusing a liquid to a patient.

In this regard, only when actuating the closure element for moving it from its closed position into its opened position, the valve device is opened. If the closure element, after opening the valve device, is no longer actuated, i.e. held in its opened position, the valve device preferably closes automatically.

The closure element preferably at least partially is formed elastically. The closure element for example may be formed in one piece from silicon rubber, whereas the housing beneficially is formed from rigid plastics or other rigid materials.

In a specific embodiment, the housing may for example comprise a first housing part and a second housing part, wherein the closure element comprises a planar section which is held in a clamped fashion in between the first housing part and the second housing part. The planar section herein may be elastic such that by means of the planar section an elastic pretensioning force is provided for pretensioning the closure element towards its closed position. The planar section may have a general disc shape extending substantially perpendicularly to the displacement direction and may be clamped with an edge portion between the first housing part and the second housing part of the housing such that via the planar section the closure element is held on the housing.

The planar section furthermore may have the shape and function of a membrane for closing off the housing towards the outside. The closure element may comprise a head adjoining the planar section and extending through an opening of the first housing part. The head protrudes along the displacement direction from the planar section and reaches through the opening of the first housing part towards the outside. Herein, the planar section of the closure element may extend across the opening of the first housing part such that the planar section covers the opening on the inside of the housing for closing the opening against a fluid flow. Hence, by means of the planar section of the closure element, the housing of the valve device is closed towards the outside such that a fluid from the flow duct of the valve device cannot exit the housing through the opening of the first housing part.

The planar section hence has a twofold function: On the one hand it provides a pretensioning force for tensioning the closure element towards its closed position. On the other hand it serves as a membrane for closing off the housing in a fluid-tight manner towards the outside.

The head of the closure element preferably serves to allow for an actuation of the closure element to move it from its closed position into its opened position. For this, the head beneficially carries at least one lever for manually displacing the closure element in the displacement direction from its closed position into its opened position. By means of the at least one lever a user, for example with his fingertips, can grab the head and can pull it in the displacement direction to bring the closure element from its closed position into its opened position. The closure element hence is actuated by a applying a pulling force onto the closure element to pull it from its closed position into its opened position.

In this regard, although the closure element preferably is actuated to bring it from its closed position into its opened position by pulling on the closure element, a user not necessarily must perform such a pulling action. It is conceivable to provide a lever mechanism on the housing allowing a user to for example push a button, wherein the lever mechanism transfers the actuating force of the user into a pulling action of the closure element.

It also is conceivable that the displacement movement of the closure element is controlled automatically by a control device. For example, in particular upon integration of the valve device into a pump device such as an infusion pump, the valve device may automatically be controlled by the pump device, in particular an electronic control of the pump device.

The closure element, in one embodiment, is arranged displaceable in an access member arranged on the first housing part, wherein the access member protrudes from a surface of the first housing part towards the outside and is arranged around the head circumferentially about the displacement direction. The access member hence serves as a cage encompassing the head of the closure element such that a user is less likely to unintentionally act onto the head of the closure element and hence onto the closure element. The access member herein may guide the head of the closure element along the displacement direction, wherein the head may have a cylindrical shape (with the displacement direction pointing along the longitudinal axis of the head) and the access member may form a corresponding guide opening in which the head of the closure element is guided.

The access member surrounds the head of the closure element about the displacement direction and, because it protrudes towards the outside from the housing, protects the closure element against unintentional forces which otherwise may lead to an unintentional actuation of the valve device. To allow for a manual access to the head of the closure element for actuating the valve device, the access member, in one embodiment, comprises at least one recess through which a user, with his fingertips, can grab the head and can move it to pull the closure element out of its closed position. The at least one lever arranged on the head herein may be located in the region of the at least one recess of the access member such that, through the at least one recess, the user may access the at least one lever.

In a specific embodiment, the access member is integrally formed with the first housing part such that the first housing part and the access member are made in one piece, for example from rigid plastics.

In a further embodiment, the closure element comprises a closing section arranged on a side of the planar section opposite the head and having a circumferential edge section which in the closed position abuts an abutment face of the housing surrounding a duct opening of the flow duct. By means of the closing section, the closure element, in its closed position, closes off the flow duct such that no fluid flow can pass through the flow duct from the inlet port towards the outlet port. The closing section, via its circumferential edge section, herein in the closed position abuts the abutment face encircling the duct opening of the flow duct, such that via the fluid-tight abutment of the edge section on the abutment face the closing section of the closure element closes off the flow duct. Beneficially, the closing section of the closure element herein is formed elastically, for example of silicon rubber, such that a fluid-tight closing of the flow duct may be achieved in a beneficial manner.

The edge section of the closing section may have the shape of a sealing lip extending radially outwards with respect to the displacement direction. The closing section herein may have a disc shape for closing off the generally circular duct opening of the flow duct in the closed position.

The closure element serves to prevent a fluid flow from the inlet port towards the outlet port in its closed position. Herein, the closing section of the closure element preferably abuts the abutment face of the housing in a flow direction, the flow direction pointing along the flow duct from the inlet port towards the outlet port. A fluid flow entering the housing through the inlet port hence presses onto the closing section, thus acting onto the closing section for holding it in its closed position.

An opposite fluid flow, i.e. a fluid flow entering the housing via the outlet port, in this regard potentially may pass the closure element if the force applied by such opposite fluid flow onto the closure element is larger than the pretensioning force by which the closure element is held in its closed position. In case of an opposite fluid flow, the valve device hence may open due to the opposite fluid flow alone if the opposite fluid flow causes a fluid pressure larger than a threshold determined by the pretensioning force of the closure element.

In case of the fluid flow entering the housing via the inlet port, the fluid flow, in the closed position of the closure element, acts both on the closed section closing off the duct opening of the fluid duct and on the planar section closing off the opening of the first housing part through which the head of the closure element extends. The action of the fluid flow on the planar section herein causes a force in an opening direction towards opening the closure element, whereas the fluid flow acting onto the closing section causes an opposite force towards holding the closure element in its closed position.

In order to make sure that the closure element is securely held in its closed position for blocking a fluid flow entering the housing via the inlet port, in one embodiment the diameter of the closing section is larger than the diameter of the opening of the first housing part through which the head extends. Because the diameter of the closing section is larger than the diameter of the opening of the first housing part through which the head extends, the surface area of the closing section onto which the fluid flow acts is larger than the surface area of the planar section onto which the fluid flow acts for causing a force towards opening the closure element. The closure element hence is held in its closed position in a self-enhancing fashion in that the force acting onto the closure element towards the closed position is larger than the force acting towards the opened position such that a net force onto the closure element towards the closed position results.

In a further embodiment the housing device may comprise an actuating mechanism with at least one movable actuation element arranged on the housing, the at least one actuation element being actuatable for displacing the closure element along the displacement direction. By such additional actuation mechanism, which is provided in addition to the closure element, an easy, comfortable actuation of the closure element in particular for opening the closure element may be achieved. The actuating mechanism serves to actuate the closure element and for this for example may manually be actuated to displace the closure element from its closed position into its opened position.

The actuating mechanism may for example comprise a lever member which is pivotably arranged on the housing. The lever member for example has a support section which abuts the housing at a pivot point about which the lever member may be pivoted relative to the housing. The housing furthermore may comprise a spring element which for example may be formed in one piece with a housing section (for example made from plastics). Such spring element beneficially pretensions the lever member into a rest position and, upon actuating the lever member, provides a resetting force for reversing the lever member into its rest position.

Just as well, the actuating mechanism may comprise a pull strap shaped as a loop which may be grapped by a user for displacing the closure element. Or the actuating mechanism may comprise magnets or other elements which may be actuated for displacing the closure element.

The valve device, in one embodiment, may be integrated into a medical system, such as an infusion line or a medical pump. The valve device described herein may however also be integrated into other medical devices which make use of a valve device for selectively cutting off a fluid flow.

The object is also achieved by means of a method for operating a valve device for a medical system, the valve device comprising:
- a valve housing,
- an inlet port arranged on the valve housing,
- an outlet port arranged on the valve housing,
- a flow duct extending through the valve housing connecting the inlet port and the outlet port to allow for a fluid flow through the valve housing between the inlet port and the outlet port and
- a closure element arranged on the valve housing for selectively opening and closing the flow duct.

Herein the closure element is displaced along a displacement direction relative to the valve housing between a closed position in which the flow duct is closed for preventing a fluid flow from the inlet port to the outlet port and an opened position in which the flow duct is opened for allowing a fluid flow from the inlet port to the outlet port, wherein the closure element is elastically pretensioned towards the closed position.

The advantages and advantageous embodiments described above for the valve device equally apply also to the method for operating the valve device, such that it shall be referred to the above.

BRIEF DESCRIPTION OF THE DRAWINGS

The idea underlying the invention shall substantially be described in more detail with regard to the embodiments shown in the figures. Herein:

FIG. 2 shows a sectional view along line A-A in FIG. 1;

FIG. 3 shows a sectional view along line B-B in FIG. 1;

FIG. 4C, 4D show sectional views of the valve device along line A-A according to FIG. 1 in the closed position;

DETAILED DESCRIPTION OF EMBODIMENTS

Figure 1:
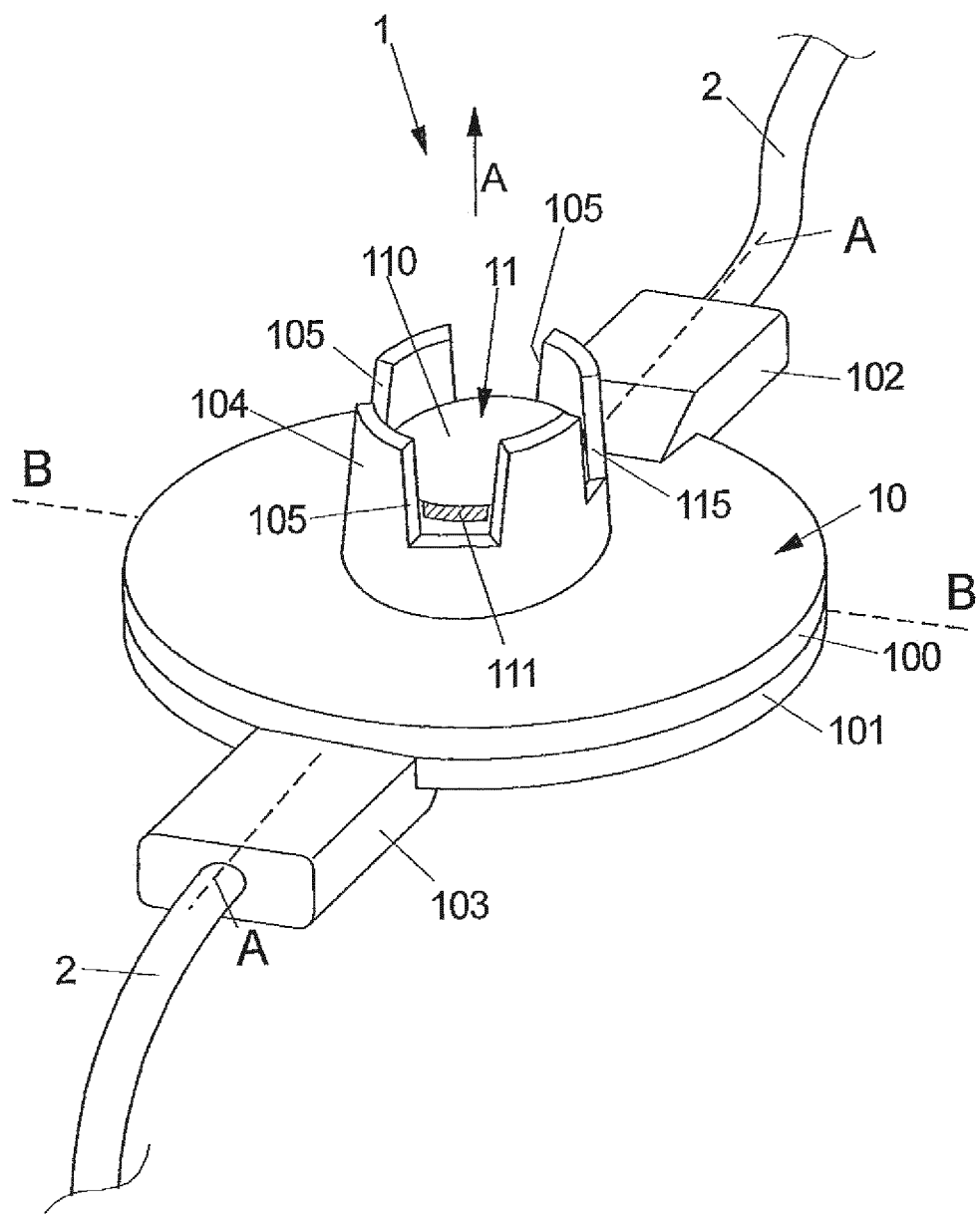
FIG. 1 shows a schematic view of a valve device.

FIG. 1 shows an embodiment of a valve device 1 arranged on an infusion line 2. The valve device 1 comprises a housing 10 having an inlet port 102 and an outlet port 103. The infusion line 2 is connected on the one hand to the inlet port 102 and on the other hand to the outlet port 103 such that for example a liquid to be infused into a patient may enter the valve device 1 via the inlet port 102 and may exit the valve device 1 via the outlet port 103.

The infusion line 2 may be part of an infusion set through which a liquid such as a salt solution, a medical drug or the like may be infused into a patient, which however is only a matter of example. In principle the valve device 1 may be used on any line or duct of a medical device for transporting a medical fluid.

The valve device 1, as can be seen from FIG. 2, comprises a housing 10 having a first housing part 100 and a second housing part 101 which are arranged and fixed on each other and in a clamping fashion hold a closure element 11. The closure element 11 comprises a planar section 112 which extends substantially perpendicularly to a displacement direction A along which the closure element 11 can be displaced relative to the housing 10. The planar section 112 has a general disc shape whose circumferential edge is clamped in between the first housing part 100 and the second housing part 101 of the housing 10.

The closure element 11, which is made in one piece of for example silicon rubber, furthermore comprises a head 110 adjoining the planar section 112 on a first side and a closing section 113 adjoining the planar section 112 on a second side opposite to the first side. The head 110 extends through an opening 106 of the first housing part 100 of the housing 10 and reaches into an access member 104 which in a cage-like manner is arranged on the first housing part 100 and protrudes from a surface 109 of the first housing part 100 towards the outside of the housing 10. The access member 104 surrounds the head 110 of the closure element 11 about the displacement direction A, as can be seen from FIG. 1, and comprises a number of recesses 105 (in the example for recesses 105) which are equally spaced and sectionally open the access member 104 in the circumferential direction about the displacement direction A such that a user may access the levers 111 arranged on the head 110 in the region of the recesses 105 for actuating the closure element 11.

The closing section 113 opposite the head 110 serves to close off a duct opening 107 on a flow duct 12 extending through the housing 10 between the inlet port 102 and the outlet port 103. The closing section 113 herein comprises a circumferential edge section 114 in the shape of a sealing lip extending radially outwards with respect to the displacement direction A and abutting in a closed position of the closure element 11—as shown in FIG. 2—on an abutment face 108 on the second housing part 101 of the housing 10. By means of the fluid-tight abutment of the edge section 114 of the closing section 113 on the abutment face 108 the duct opening 107, in the closed position of the closure element 11, is closed such that no fluid can flow from the inlet port 102 towards the outlet port 103 through the flow duct 12.

The closure element 11 is formed in one piece for example of silicon rubber. At least the planar section 112 and the closing section 113 herein are elastic such that via the planar section 112 the closure element 11 is held in its closed position in an elastically pretensioned fashion, while the closing section 113 via its edge section 114 resiliently abuts the abutment face 108 of the housing 10. In the normal, non-actuated state the closure element 11 is thus in its closed position in which the edge section 114 of the closing section 113 is in fluid-tight abutment with the abutment face 108 surrounding the duct opening 107.

Figure 4A:
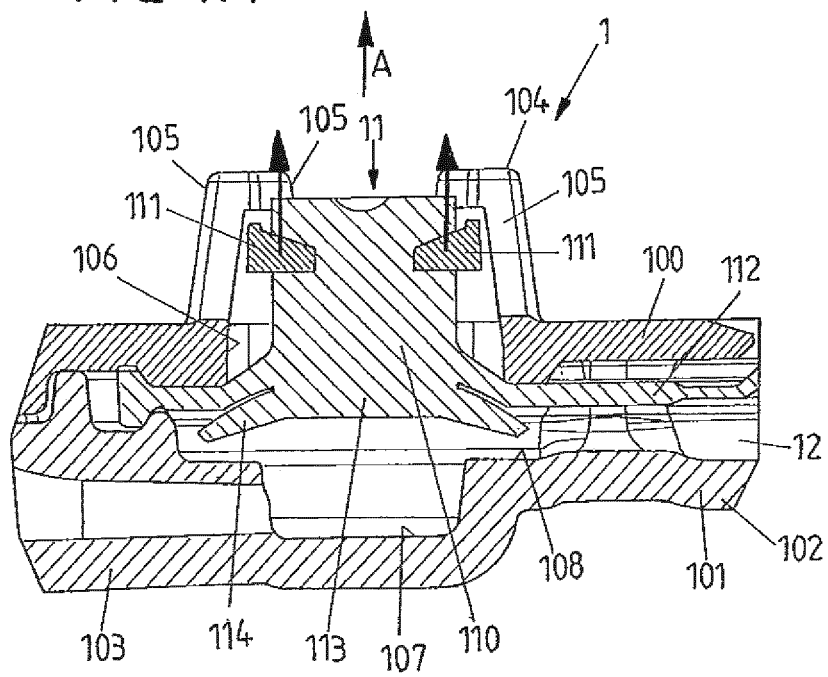
FIG. 4A, 4B show sectional views of the valve device along line A-A according to FIG. 1 in the opened position.
Figure 4B:
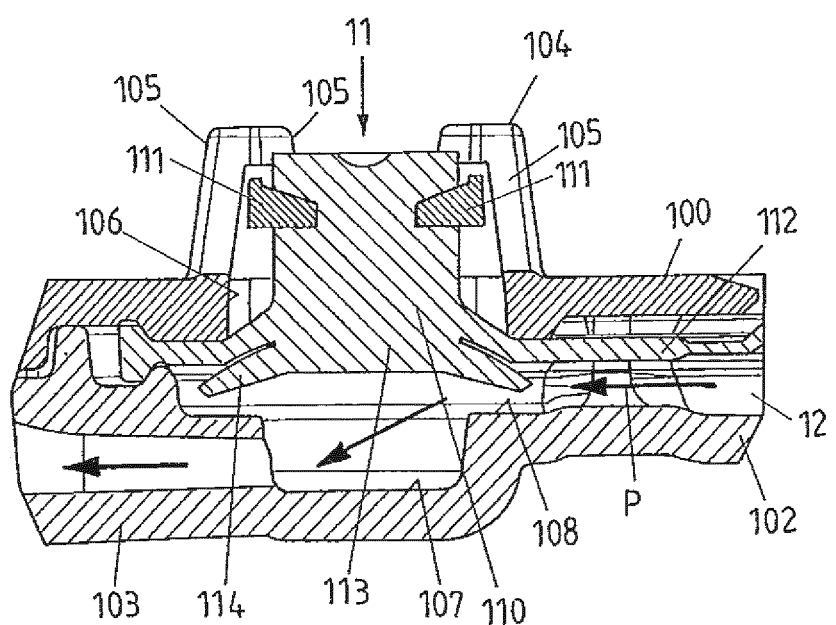

For opening the valve device 1 a user may access the head 110 of the closure element 11 through the recesses 105 of the access member 104 by means of his fingertips. By pulling on the levers 111 the closure element 11 hence may be pulled in the displacement direction A from its closed position into an opened position in which the flow duct 12 is opened, hence allowing for a fluid flow P through the flow duct 12, as indicated in FIGS. 4A and 4B. A user hence may manually act onto the closure element 11 for pulling it into its opened position for opening the valve device 1. By holding the closure element 11 in its opened position fluid is allowed to pass through the flow duct 12 and hence through the infusion line 2 (see FIG. 1).

Once a user releases the closure element 11, it automatically—due to the pretensioning force of the planar section 112 caused by the deformation of the planar section 112 when opening the closure element 11 as indicated in FIGS. 4A and 4B—is moved back in its closed position, as shown in FIGS. 4C and 4D. If no actuation force acts onto the closure element 11, the closure element 11 hence assumes its closed position in which the flow duct 12 is closed and no fluid can pass from the inlet port 102 to the outlet part 103. The infusion line 2 hence is cut off.

In the embodiment shown in the FIGS. 1 to 4 the closure element 11 can be actuated to move it from its closed position into its opened position by pulling on the head 110. In this regard it is also conceivable that a suitable lever mechanism or the like is provided such that a user may for example push a button or actuate another suitable actuating element, wherein the lever mechanism transfers the actuating movement into a pulling movement of the closure element 11.

The closure element 11 may also be actuated in a controlled fashion by means of an electronic control device. For example, the valve device 1 may be controlled by a pump device, for example an infusion pump, such that the pumping action of the pump device may be synchronized with a selective opening or closing of the valve device 1.

The planar section 112 extends in a disc-like fashion and acts as a membrane for closing of the opening 106 against a fluid flow towards the outside. For this, the planar section 112 fully covers the opening 106 in a fluid-tight manner. In the closed position of the closure element 11, as indicated in FIG. 4C, a fluid flow P entering via the inlet port 102 into the valve device 1 causes a pressure force F1 on the circumferential edge section 114 of the closing section 113 and a pressure force F2 on the planar section 112 in the region of the opening 106. Herein, the force F1 due to the pressure of the fluid flow P acting onto the edge section 114 of the closing section 113 points in a direction towards closing the closure element 11, hence enhancing the holding of the closure element 11 in its closed position. In contrast, the force F2 due to the pressure of the fluid flow P acting onto the planar section 112 in the region of the opening 106 points in a direction towards opening the closure element 11, thus acting against the forces holding the closure element 11 in its closed position. If the diameter D1 of the closing section 113 in its closed position is larger than the diameter D2 of the opening 106, as indicated in FIG. 4C, the force F1 acting in the closing direction exceeds the force F2 acting in the opening direction, such that the closure element 11 in a self-enhancing fashion is held in its closed position.

In this regard it is to be noted that the closing section 113 and the opening 106 may have a generally circular shape. The head 110 extending through the opening 106 may have a cylindrical shape, with the displacement direction A pointing along the longitudinal axis of the head 110.

The closure element 11, in its closed position, closes off the duct opening 107 such that the valve device 1 is closed against a fluid flow P from the inlet port 102 to the outlet port 103. Hence, in a forward direction pointing from the inlet port 102 to the outlet port 103 the valve device 1 is closed by the edge section 114 of the closing section 113 abutting the abutment face 108 of the housing 10 in the forward direction. As shown in FIG. 4D, in the backward direction however a fluid flow P entering the valve device 1 via the outlet port 103 can pass the flow duct 12 towards the inlet port 102 if the pressure caused by the opposite fluid flow P onto the closing section 113 of the closure element 11 in the backward direction exceeds the pretensioning force by which the closure element 11 via its planar section 112 is held in its closed position. If the pressure caused by the backward flow exceeds the threshold determined by the pretensioning force, the closure element 11 is pushed in the displacement direction A for allowing a fluid flow P towards the inlet port 102, wherein the closure element 11 automatically closes again once the pressure caused by the backward flow falls again under the threshold.

The valve device 1 as described herein may in a beneficial manner be integrated into medical devices such as an infusion line 2. The valve device 1 herein may be produced in a cheap manner such that a disposable infusion line 2 with a valve device 1 arranged thereon may be provided.

The structure of the valve device 1 allows for integration in a miniaturized form in small medical devices. For example, as indicated in FIG. 3, the planar section 112 may have a thickness of 0.5 mm, the head 110 may have a diameter of 3.4 mm, the access member 104, at its tip, may have a diameter of 5.45 mm, the duct opening 107 may have a diameter of 3.82 mm, and the edge section 114 of the closing section 113 may have a diameter of 6.12 mm. It is to be understood that this is just an example. Of course, also other dimensions of the parts of the valve device 1 are conceivable and equally possible dependent on the specific use of the valve device 1.

Figure 5A:
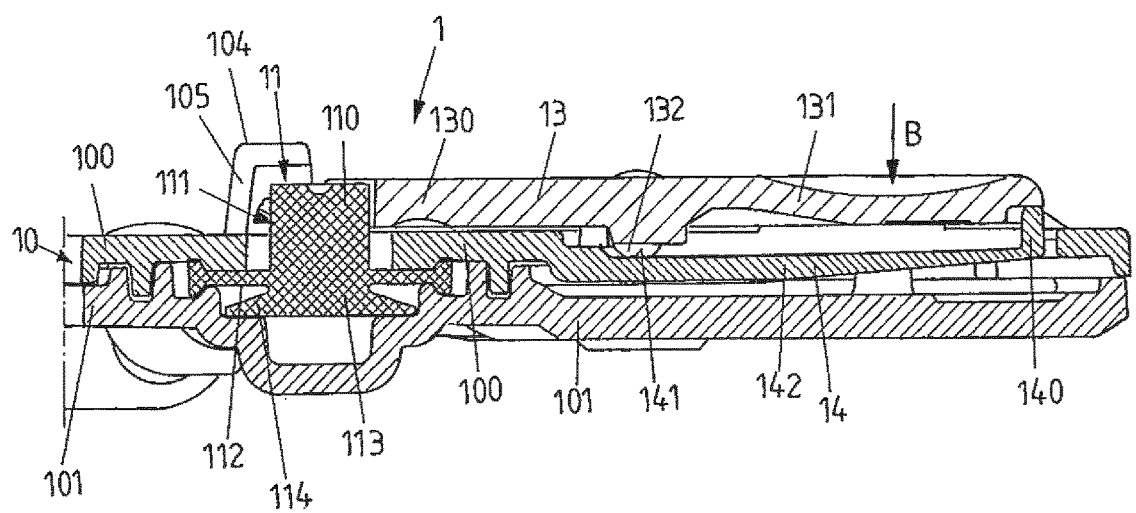
FIG. 5A shows a sectional view of an embodiment of a valve device including an actuating mechanism comprising an actuation element shaped as a lever member, in a non-actuated state.
Figure 5B:
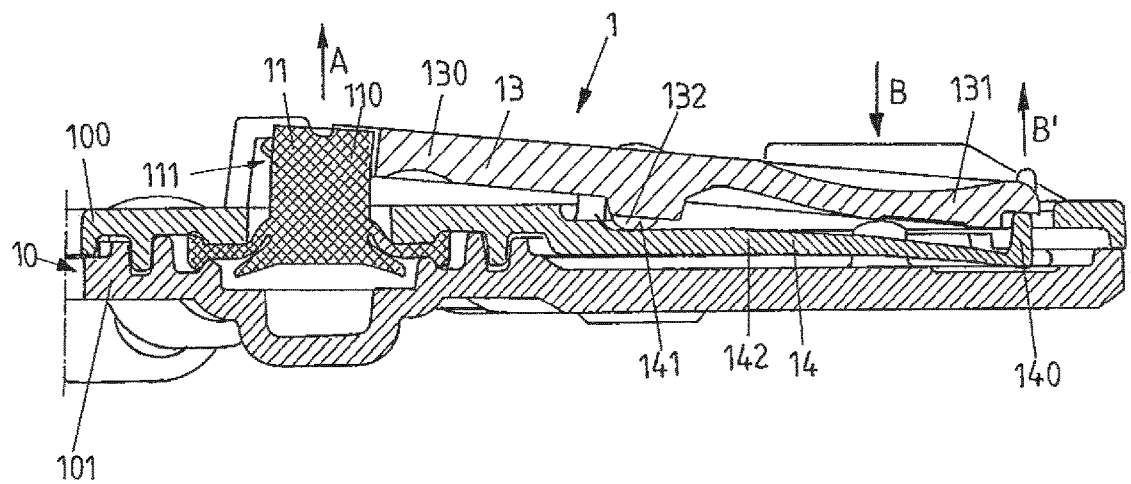
FIG. 5B shows the embodiment of FIG. 5A, in an actuated state.

FIGS. 5A and 5B show an embodiment of a valve device 1 in which on a housing 10 an actuating mechanism comprising an actuating lever member 13 is arranged. The lever member 13 comprises an engagement section 130 which is in engagement with the closure element 11. The lever member 13 furthermore comprises an actuation section 131 which may manually be actuated for displacing the closure element 11. The engagement section 130 and the actuation section 131 extend towards different directions from a support section 132 which abuts the first housing part 100 of the housing 10 on a pivot point 141 such that the lever member 13 is pivotable about the support section 132 with respect to the housing 10.

The support section 132, in cross section, has a round shape such that the lever member 13 may be pivoted about the support section 132 with respect to the first housing part 100 of the housing 10.

For actuation a user presses into an actuation direction B onto the actuation section 131 such that the actuation section 131 is pressed towards the housing 10 (downwards in FIGS. 5A and 5B). Hence, the lever member 13 is pivoted about the support section 132 such that the engagement section 130 moves upwards in the displacement direction A. The engagement section 130 is, via an actuation lever 111 on the closure element 11, in engagement with the closure element 11. Due to the engagement the closure element 11 is moved upwards in the displacement direction A together with the engagement section 130 of the lever member 13. Hence, as shown in FIG. 5B, the closure element 11 is moved towards its open position, and the valve device 1 is opened.

The upwards movement of the closure element 11 in the displacement direction A is limited by an end stop provided by the access member 104. As shown in FIG. 5B, the engagement section 130 of the lever member 13 abuts on the upper edge of the access member 104 with its end such that the lever member 13 cannot be pivoted further.

Formed in one piece with the first housing part 100 is a spring element 14 which at least sectionally is elastic and joined with the first housing part 100 at an end 142. The spring element 14, by means of an engagement section 140 at an end opposite the end 142, is in engagement with the actuation section 131 of the lever member 13. When the lever member 13 is actuated by moving the actuation section 131 in the actuation direction B the spring element 14 is tensioned, due to the engagement section 140 being pressed downwards and hence deforming the spring element 14. Due to the deformation of the spring element 14, a reverse force in a reverse direction B' is provided, which serves to reset the lever member 13 towards its initial rest position (FIG. 5A).

The idea underlying the invention is not limited to the embodiments described above, but may be used also in entirely different embodiments.

In particular, a valve device as described herein may also be integrated into other medical devices than the ones mentioned in this text and may be used also for other purposes than infusion, for example transfusion or enteral feeding or the like.

LIST OF REFERENCE NUMERALS

1 Valve device
10 Housing
100, 101 Housing part
102 Inlet port
103 Outlet port
104 Access member
105 Recess
106 Opening
107 Duct opening
108 Abutment face
109 Surface
11 Closure element
110 Head
111 Actuating element
112 Planar section
113 Closing section
114 Circumferential edge
12 Flow duct
13 Actuation element (lever member)
130 Engagement section
131 Actuation section
132 Support section
14 Spring element
140 Engagement section
141 Pivot point
142 End
2 Line
A Displacement direction
B Actuation direction
B' Reverse direction
D1, D2 Diameter
F1, F2 Force
P Fluid flow

What is claimed is:

1. A valve device for a medical system, comprising:
a valve housing,
an inlet port arranged on the valve housing,
an outlet port arranged on the valve housing,
a flow duct extending through the valve housing connecting the inlet port and the outlet port to allow for a fluid flow through the valve housing between the inlet port and the outlet port, and
a closure element arranged on the valve housing for selectively opening and closing the flow duct,
wherein the housing comprises a first housing part and a second housing part, wherein the closure element comprises an elastic planar section which is held in a clamped fashion in between the first housing part and the second housing part,
wherein the closure element is displaceable along a displacement direction relative to the valve housing between a closed position in which the flow duct is closed for preventing the fluid flow from the inlet port to the outlet port and an opened position in which the flow duct is opened for allowing the fluid flow from the inlet port to the outlet port, wherein the closure element is elastically pretensioned to move axially into the closed position by the elastic planar section,
wherein the closure element comprises a head adjoining the planar section and extending through an opening of the first housing part so as to be configured to be accessible from an exterior of the housing,
wherein the planar section extends, in the closed position, substantially perpendicularly to the displacement direction and is configured to cover the opening so as to prevent the fluid flow into the opening, wherein the closure element is actuatable to move the closure element from the closed position into the opened position by pulling on the head.

2. The valve device according to claim 1, wherein the head carries at least one lever for manually displacing the closure element in the displacement direction from the closed position into the opened position.

3. The valve device according to claim 1, wherein the closure element is arranged displaceably in an access member arranged on the first housing part, wherein the access member protrudes from a surface of the first housing part and is arranged around the head circumferentially about the displacement direction.

4. The valve device according to claim 3, wherein the access member comprises at least one recess for providing access to the head for actuating the closure element.

5. The valve device according to claim 3, wherein the first housing part is integrally formed with the access member.

6. The valve device according to claim 1, wherein the closure element comprises a closing section arranged on a side of the planar section opposite the head and having a circumferential edge section which in the closed position abuts an abutment face of the housing surrounding a duct opening of the flow duct.

7. The valve device according to claim 6, wherein a diameter of the closing section is larger than a diameter of the opening of the first housing part through which the head extends.

8. The valve device according to claim 6, wherein the edge section of the closing section extends circumferentially about the displacement direction.

9. The valve device according to claim 1, wherein the housing comprises an actuating mechanism with at least one movable actuation element arranged on the housing, the at least one actuation element being actuatable for displacing the closure element along the displacement direction.

10. The valve device according to claim 9, wherein the at least one actuation element is formed as a pivotable lever member arranged pivotably on the housing and comprising an engagement section being in engagement with the closure element.

11. A medical system, comprising the valve device according to claim 1.

12. The valve device according to claim 1 wherein the closure element is a one-piece structure including the head and the planar section.

13. The valve device according to claim 1 wherein the closure element includes a waist section and a closing section having a circumferential edge section in a shape of a sealing lip extending radially outwards with respect to the displacement direction and the waist section in both the opened and closed positions, said circumferential edge section being spaced in the displacement direction from the planar section of the closure element by the waist section so that an annular recess is formed so that the closure element and the housing are configured so that the fluid flow into the housing through the inlet port enters the annular recess and causes a pressure force on the circumferential edge section so as to enhance holding of the closure element in the closed position.

14. The valve device according to claim 1 wherein the elastic planar section of the closure element includes a top surface that extends substantially perpendicularly to the displacement direction and a bottom surface that extends substantially perpendicularly to the displacement direction, and wherein the elastic planar section is held in the clamped fashion by the first housing part engaging the top surface of the elastic planar section and the second housing part engaging the bottom surface of the elastic planar section.

15. A method for operating a valve device for a medical system, the method comprising the steps of:
providing the valve device comprising a valve housing, an inlet port arranged on the valve housing, an outlet port arranged on the valve housing, a flow duct extending through the valve housing connecting the inlet port and the outlet port to allow for a fluid flow through the valve housing between the inlet port and the outlet port, and a closure element arranged on the valve housing for selectively opening and closing the flow duct,
operating the valve device by a user directly or indirectly engaging a head portion of the closure element from an exterior of the housing and manually displacing the closure element by pulling the closure element along a displacement direction relative to the valve housing from a closed position in which the flow duct is closed for preventing the fluid flow from the inlet port to the outlet port to an opened position in which the flow duct is opened for allowing the fluid flow from the inlet port to the outlet port, wherein the closure element is elastically pretensioned to move axially into the closed position by an elastic planar section of the closure element that is clamped within the valve housing.

* * * * *